United States Patent [19]

Pelosi et al.

[11] 4,072,144
[45] Feb. 7, 1978

[54] INSTRUMENT AND METHOD FOR MEASURING URETHRAL DEFECTS IN PATIENTS WITH URINARY STRESS INCONTINENCE

[76] Inventors: Marco Antonio Pelosi, 182 Springfield Ave., Berkeley Heights, N.J. 07922; Joseph J. Apuzzio, 1005 Fanny St., Elizabeth, N.J. 07201

[21] Appl. No.: 651,210

[22] Filed: Jan. 21, 1976

[51] Int. Cl.² .............................................. A61B 5/10
[52] U.S. Cl. ................................. 128/2 S; 33/174 D
[58] Field of Search ....................... 128/2 S, 2 R, 361; 33/174 D

[56] References Cited

U.S. PATENT DOCUMENTS

| 1,186,552 | 6/1916 | Cohen et al. ............... 33/174 D X |
| 1,571,140 | 1/1926 | O'Connor ..................... 33/174 D |
| 2,052,452 | 8/1936 | De Jarnette .................. 33/174 D |
| 3,097,637 | 7/1963 | Horton ............................. 128/2 |

FOREIGN PATENT DOCUMENTS

| 844,040 | 7/1952 | Germany ..................... 33/174 D |
| 11,910 of | 1897 | United Kingdom ............ 128/361 |
| 136,161 | 1/1921 | United Kingdom ............ 128/2 R |

Primary Examiner—Kyle L. Howell
Attorney, Agent, or Firm—Silverman & Jackson

[57] ABSTRACT

The present method involves the use of a urethral probe, having one tapered end with a silk thread anchored near said tapered end, at about 4 centimeters from the apex of the taper. The probe is inserted into the urethra while the free end of the thread is held firmly in the examiner's hand. Once the probe has been inserted into the urethra to the point where the attachment of the string is exactly at the external meatus, the examiner holds only the thread, exerting a slight tension on it. (The thread represents a continuation of the unstrained urethral axis.) The patient is then asked to strain. If there is any weakness of urethral support, the instrument is deflected upward. This upward deflection causes the stationary thread to create an angle which is then read directly from a scale, wherein the degree of deflection can be interpretively read in order to determine the degree of deformity of the urethrovesical angle from its normal anatomic position.

3 Claims, 5 Drawing Figures

INSTRUMENT AND METHOD FOR MEASURING URETHRAL DEFECTS IN PATIENTS WITH URINARY STRESS INCONTINENCE

BACKGROUND OF THE INVENTION

During the past 25 years, a number of important innovations have been made in the diagnosis of urinary stress incontinence. Whereas, in the past, the emphasis was upon surgical approaches to problems in this area, such thinking has, with advances in the field, undergone substantial change.

It is now important to evaluate the patient preoperatively, with an objective investigation, to determine the degree of anatomic abnormality present so that an appropriate choice of surgical approach can be made at the outset.

The introduction of the chain cystourethrogram has proved to be an important diagnostic aid in the evaluation of patients with urinary stress incontinence. With this technique, the posterior urethrovesical angle and the urethral axis can be investigated easily, and a rational method of operative repair selected for each patient.

Green, in 1963, identified two basic anatomic defects as causing stress incontinence. In type I, the posterior urethrovesical angle is lost, but the inclination of the urethral axis is maintained at at least a 45° angle to the vertical. Symptomatology in patients with type I defects ranges from mild to moderate incontinence and is managed by restoring the posterior urethrovesical angle by anterior colporrhaphy. In a type II deformity, not only is the posterior urethrovesical angle lost, but the urethral axis is rotated posteriorly past 45° to the vertical. This rotation of the urethral axis can be demonstrated quite accurately in a chain cystourethrogram. Patients having type II stress incontinence often exhibit severe symptoms and usually require a retropubic urethropexy rather than an anterior colporrhaphy to effect a cure.

In 1971, Crystle et al reported the "Q-tip test" as a simple means of differentiating between type I and type II defects: When a cotton-tipped applicator is inserted into the bladder neck, the patient is asked to strain, the free end of the applicator stick develops an arc directly opposite to the arc formed by the end of the stick within the urethra. The degree of rotation of the stick's free end was found to correlate well with the degree of the axis rotation of the urethra, as observed on the chain cystourethrogram. Similar results have been reported by Reynolds and Miller.

In the above approach, a significant degree of guesswork was necessitated in attempting to estimate the degree of axis rotation formed by the end of the cotton-tipped applicator.

The present invention represents a response to the needs which were evidenced by the shortcomings in the above-described prior art efforts.

SUMMARY OF THE INVENTION

It is an object of the present invention to provide a diagnostic device for stress incontinence which is accurate, simple in construction, and easily utilized.

The present method involves the use of a urethral probe, having one tapered end with a silk thread anchored near said tapered end, at about four centimeters from the apex of the taper. The probe is inserted into the urethra while the free end of the thread is held firmly in the examiner's hand. Once the probe has been inserted into the urethra to the point where the attachment of the string is exactly at the external meatus, the examiner holds only the thread, exerting a slight tension on it. (The thread represents a continuation of the unstrained urethral axis.) The patient is then asked to strain. If there is any weakness of urethral support, the instrument is deflected upward. This upward deflection causes the stationary thread to create an angle which is then read directly from a scale, wherein the degree of deflection can be interpretively read in order to determine the degree of deformity of the urethrovesical angle.

DETAILED DESCRIPTION OF THE INVENTION

Figure 1:
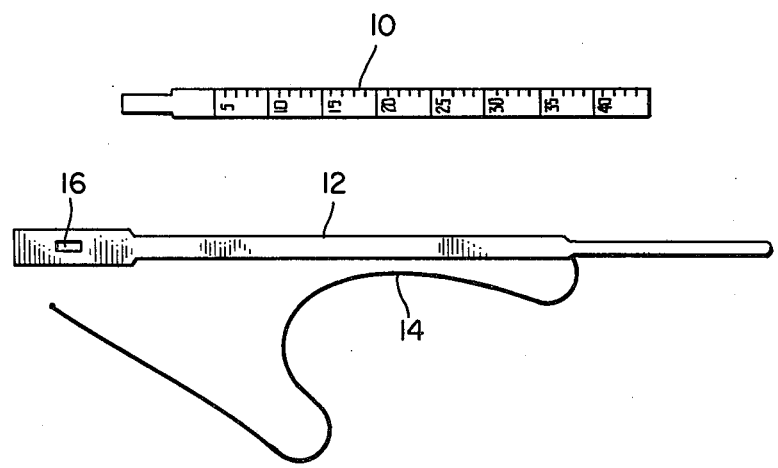
FIG. 1 is a top-perspective view of the urethral probe showing a thread attached near the tapered end; also shown is the calibration rod.
Figure 2:
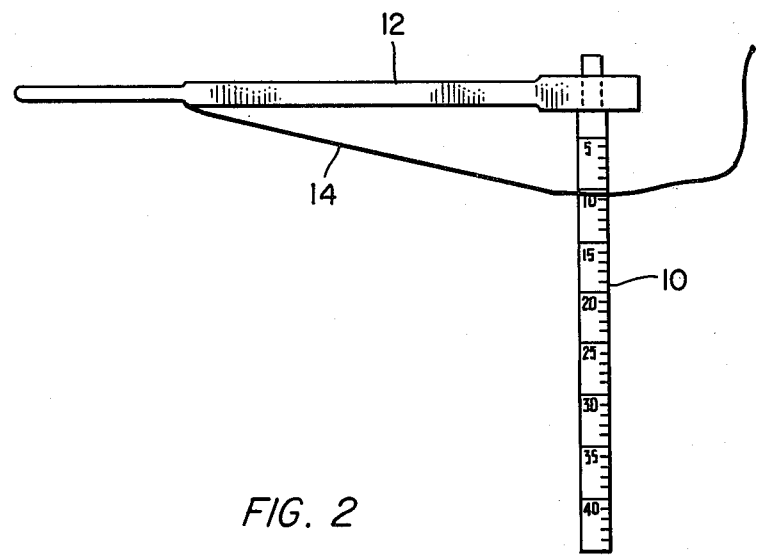
FIG. 2 is a top-perspective view of the urethral probe and the calibration rod joined together in a manner in which the angle of rotation of the urethral axis may be measured.

Referring to FIG. 1, it is seen that the instrument is constructed of two light plastic rods 10 and 12, each having a diameter of about 4 milimeters. The rod 12 is about 13 centimeters long and is tapered at one end in order to form the urethral probe. A silk thread 14 is anchored to the tapered end of the urethral probe 12 at 4 centimeters from the apex or end of the probe. At the other end of the rod 12 is a small groove 16 which permits the measuring rod 10 to fit snugly at right angles to the rod 12. (See FIG. 2). Said rod 10 is about 9 centimeters long and has imprinted upon it a scale of angles ranging from 0° to 45°. It is attached to rod 12 at a point about 9 centimeters from the silk string 14.

Figure 3:
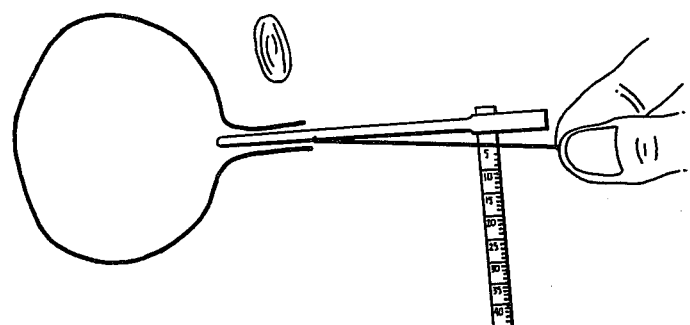
FIG. 3 is a schematic view showing the measurement of the angle of the urethral axis as it appears in a normal state.
Figure 4:
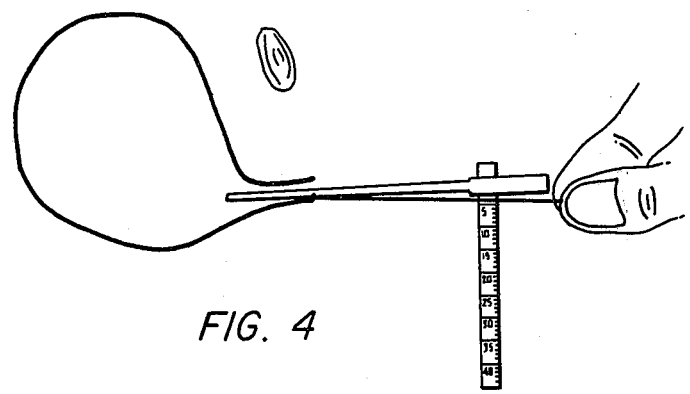
FIG. 4 is a schematic view of the angle of the urethral axis as it appears in a type I defect.
Figure 5:
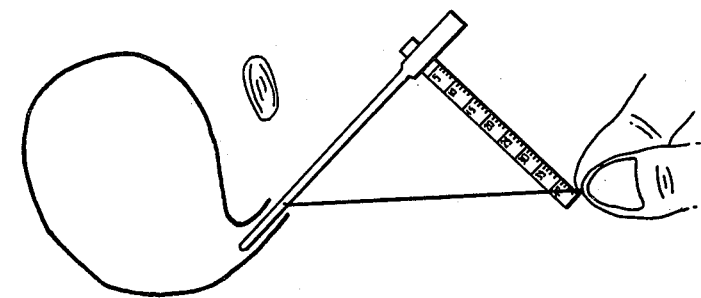
FIG. 5 is a schematic view showing the manner of measurement of the angle of the urethral axis where a type II defect is present.

In order to utilize the present diagnostic device, the patient is placed in a lithotomy position. The instrument is then assembled, and the urethral probe coated with lidocaine jelly, so as to minimize possible discomfort to the patient. The probe is then inserted into the urethra, to the opening of the bladder, (FIGS. 3, 4, and 5).

The free end of the thread is then held firmly in the examiner's hand. The instrument is then ready for use. Once the probe 12 has been inserted into the urethra to the point where the attachment of the string is exactly at the external meatus, the examiner holds only the thread, exerting a slight tension on it.

The thread represents a continuation of the unstrained urethral axis. The patient is then asked to strain, that is, to tense his muscles in the urethral area. If there exists any weakness of urethral support, the instrument is deflected upwards. This upward deflection causes the stationary thread to create an angle which is then read directly from the scale. Therefore, the degree of rotation of the urethral axis can be easily and accurately obtained, without guesswork as to estimation of angles.

The inventors have performed tests involving the present novel method and apparatus upon 62 patients who have undergone cystourethrograms for evaluation of urinary incontinence. The degree of axis rotation of the urethra, as seen by the chain cystourethrogram, correlates very well with the degree of rotation of the urethral probe.

More particularly, the clinical results which have been obtained are as follows:

1. When the chain cystourethrogram does not demonstrate any loss of the posterior urethrovesical angle nor any urethral axis rotation, the urethral probe remains in its nonstraining position or, alternatively, it is deflected only sightly upwards (See FIG. 3) this deflection is usually less than 10° as may be seen on printed scale 10.

2. When there exists a type I defect, the findings are the same as in patients without anatomic defects (See FIG. 4).

3. In the case of a type II defect, the urethral probe rotates above the horizontal in counter-clockwise fashion, wherein the degree of rotation will depend upon the severity of the anatomic defect (See FIG. 5). The minimum degree of change required for indication of type II defect has been established at 20°, as recorded directly from scale 10. It has been reported that where the free end of the stick rotates more than 20° from its non-straining position, a type II defect will invariably be seen on the cystourethrogram. The clinical results obtained with the present inventive method confirm this finding.

It is to be appreciated that the present novel instrument is easily constructed, disposable in nature, and is inexpensive from a manufacturing viewpoint.

The procedure for its use can be easily learned and may be readily performed in a single office visit with a minimum of discomfort to the patient. Thusly, a patient complaining of urinary stress incontinence can be easily evaluated using a vesical neck elevation test, of the Bonney or the Marshall-Marchetti type, to establish that the symptom of stress incontinence is the result of a loss of urethrovesical angle.

If this test is positive, the use of the present instrument can then be employed in order to determine whether a type I or type II defect is involved. The clinician will thereby obtain enough information in order to select the proper surgical technique for the particular patient.

It is thus seen that the objects as set forth in the Summary of the Invention have been effectively obtained by the above description.

While there have been herein shown and described the preferred embodiments of the present invention, it will be understood that the invention may be embodied otherwise than as herein specifically illustrated or described and that within said embodiments certain changes in the detail and construction, and the form and arrangement of the parts may be made without departing from the underlying idea of principles of this invention within the scope of the appended claims.

What we claim is:

1. An instrument for measuring urethral defects, comprising:
  a. a urethral probe having a taper toward one end thereof;
  b. a flexible thread anchored near the area of commencement of said tapered end to permit a positive connection forming a unitary device; and
  c. a straight calibrated measuring rod having, at one end thereof, a means for transverse securement of said rod to the end of said probe opposite to the tapered end, wherein said thread, when held by the examiner during insertion of the probe into the urethra to the opening of the bladder, represents a continuation of the unstrained urethral axis and, further wherein, any deflection of said thread which may occur upon a urethral straining by the patient, corresponds to the degree of deformity of the urethrovesical angle.

2. The instrument as recited in claim 1 in which said tapered rod is about 13 centimeters long and in which said flexible thread is anchored at about 4 centimeters from the apex of said taper.

3. The method for measuring deformity of the urethrovesical angle, comprising the steps of:
  a. placing the patient in a lithotomy position;
  b. inserting a urethral probe having a taper toward one end thereof, and a flexible thread anchored upon said probe near the area of commencement of said taper, into the meatus of the urethra to the opening of the bladder, wherein a calibrated measuring rod is transversely secured at the opposite end of said probe from said tapered end;
  c. holding said thread while the urethra is in an unstrained condition, such that said thread represents a continuation of the unstrained urethral axis;
  d. having the patient tense the muscles in the urethral area; and,
  e. reading on said calibrated rod any resultant deflection of the otherwise stationary thread which may be therein caused by said straining, wherein the degree of deflection of said thread corresponds to the degree of deformity of the urethrovesical angle.

* * * * *